(12) United States Patent
Klitgaard et al.

(10) Patent No.: US 11,266,609 B2
(45) Date of Patent: Mar. 8, 2022

(54) BACITRACIN AND/OR DAPTOMYCIN COMBINED WITH CANNABIDIOL FOR TREATMENT OF BACTERIAL INFECTIONS

(71) Applicant: Syddansk Universitet, Odense M (DK)

(72) Inventors: Janne Kudsk Klitgaard, Årslev (DK); Claes Søndergaard Wassmann, Odense SØ (DK)

(73) Assignee: Syddansk Universitet, Odense M (DK)

( * ) Notice: Subject to any disclaimer, the term of this patent is extended or adjusted under 35 U.S.C. 154(b) by 99 days.

(21) Appl. No.: 16/624,242

(22) PCT Filed: Jun. 19, 2018

(86) PCT No.: PCT/EP2018/066234
§ 371 (c)(1),
(2) Date: Dec. 18, 2019

(87) PCT Pub. No.: WO2018/234301
PCT Pub. Date: Dec. 27, 2018

(65) Prior Publication Data
US 2020/0146999 A1    May 14, 2020

(30) Foreign Application Priority Data

Jun. 19, 2017 (EP) .................................... 17176612

(51) Int. Cl.
| A61K 31/05 | (2006.01) |
| A61P 31/04 | (2006.01) |
| A61K 9/00 | (2006.01) |
| A61K 38/12 | (2006.01) |
| A61K 31/352 | (2006.01) |

(52) U.S. Cl.
CPC ............ *A61K 31/05* (2013.01); *A61K 9/0014* (2013.01); *A61K 9/0048* (2013.01); *A61K 31/352* (2013.01); *A61K 38/12* (2013.01); *A61P 31/04* (2018.01)

(58) Field of Classification Search
None
See application file for complete search history.

(56) References Cited

U.S. PATENT DOCUMENTS

| 2010/0221245 A1 | 9/2010 | Kunin |
| 2013/0011484 A1* | 1/2013 | Bevier ..................... A61K 9/14 |
| | | 424/491 |
| 2013/0302306 A1 | 11/2013 | Schuch et al. |

FOREIGN PATENT DOCUMENTS

| GB | 2542797 | 4/2017 |
| WO | WO 2007/042811 A1 | 4/2007 |
| WO | WO 2009/158499 A2 | 12/2009 |
| WO | WO 2012/144892 A1 | 10/2012 |
| WO | WO 2015/048508 A1 | 4/2015 |
| WO | WO 2016/103254 A1 | 6/2016 |
| WO | WO 2017/045060 A1 | 3/2017 |
| WO | WO 2018/085535 A2 | 5/2018 |
| WO | WO 2018/085535 A3 | 6/2018 |

OTHER PUBLICATIONS

Blaskovich et al. ("The antimicrobial potential of cannabidiol," Communications Biology (2021), 4(1), 7, pp. 1-18) (Year: 2021).*
Appendino et al., "Antibacterial cannabinoids from Cannabis saliva: a structure-activity study," *Journal of Natural Products*, 71(8): 1427-1430, 2008.
Bass et al., "A novel nonpsychotropic cannabinoid, HU-211, in the treatment of experimental pneumococcal meningitis," *Journal of Infectious Diseases*, 173(3): 735-738, 1996.
International Search Report and Written Opinion for PCT/EP2018/066234, dated Sep. 10, 2018, 13 pages.

* cited by examiner

*Primary Examiner* — Christina Bradley
(74) *Attorney, Agent, or Firm* — Klarquist Sparkman, LLP

(57) ABSTRACT

The present invention relates to compositions comprising Cannabidiol (CBD) or pharmaceutically acceptable salts thereof, and bacitracin or pharmaceutically acceptable salts thereof and/or daptomycin or pharmaceutically acceptable salts thereof. The compositions show a synergistic effect in the inhibition of growth of Gram-positive bacteria. Thus, the compositions according to the invention may e.g. find use as medicaments in the treatment of Gram-positive bacterial infections.

20 Claims, 10 Drawing Sheets

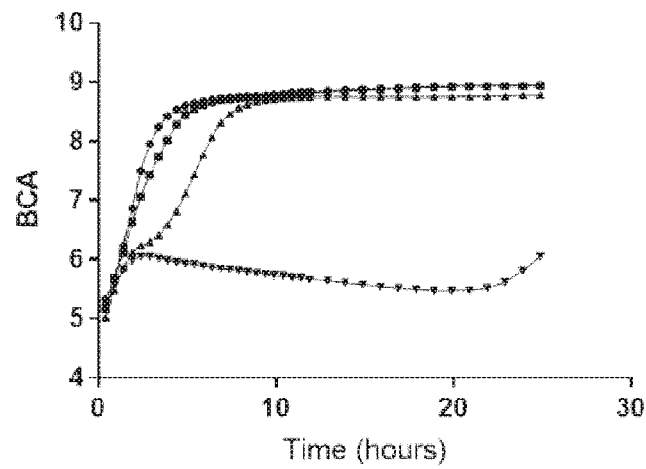
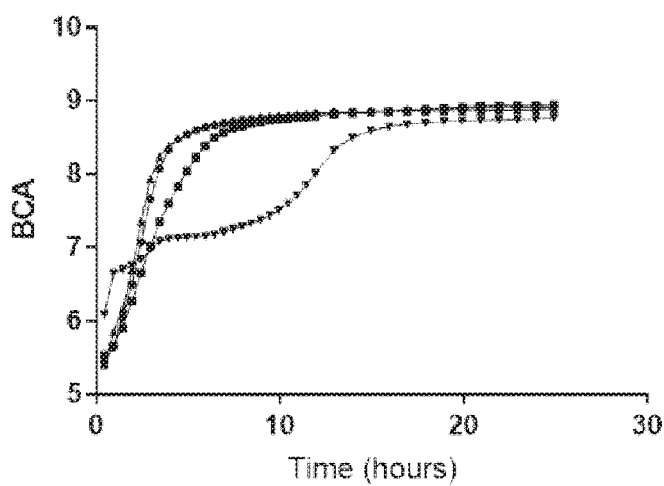
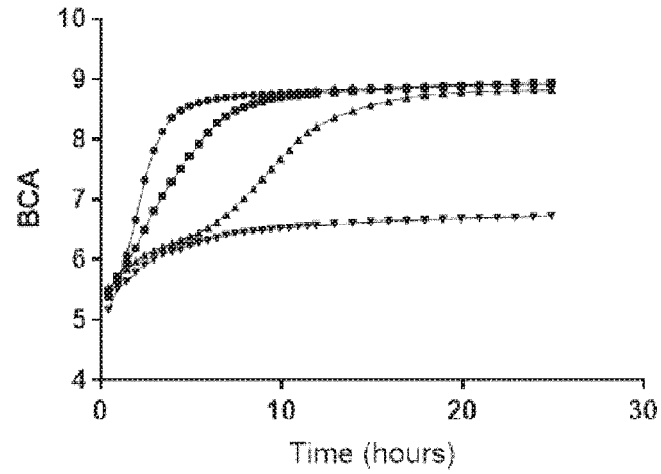
Fig. 1, continues

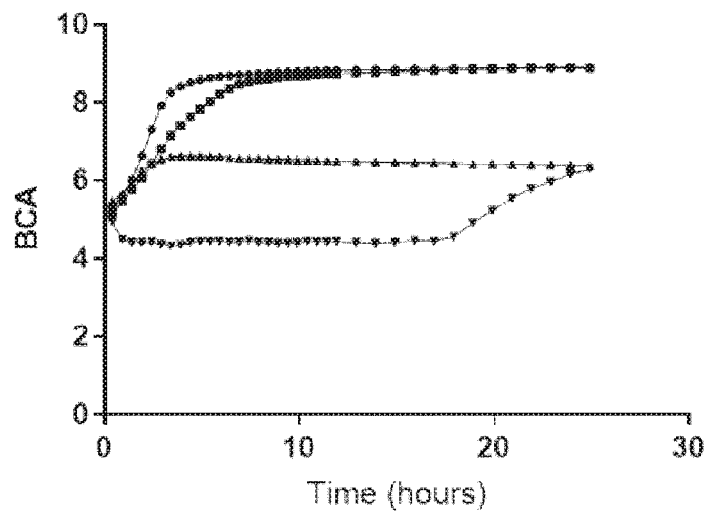
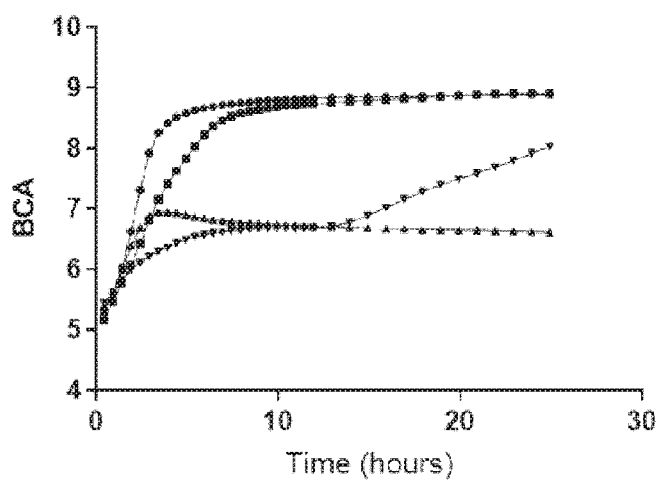
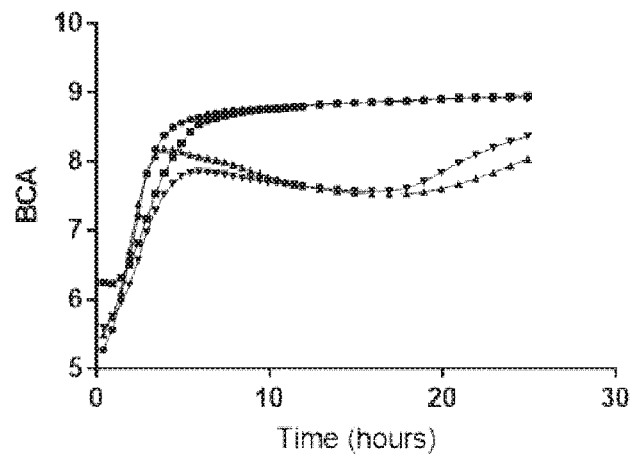
Fig. 1, continues

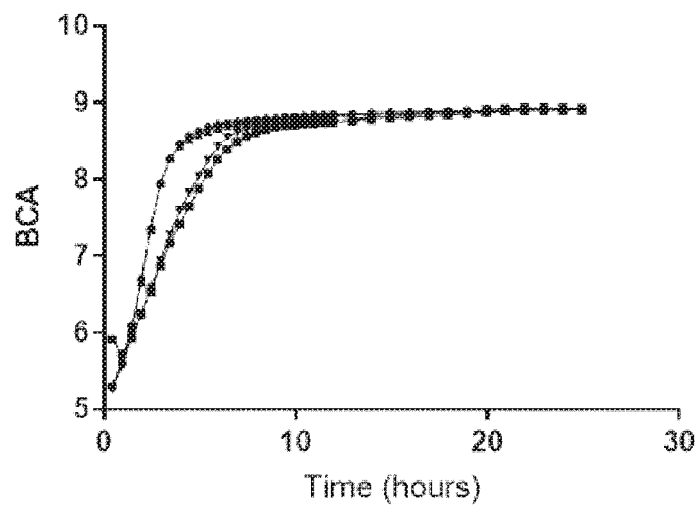
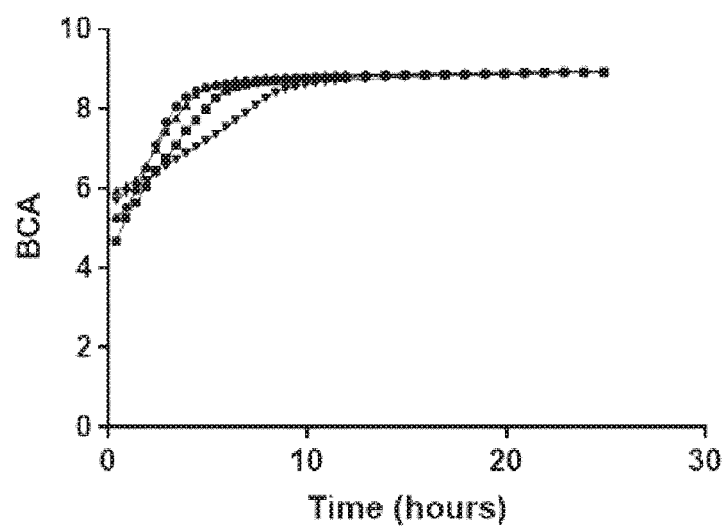
Fig. 1, continued

A
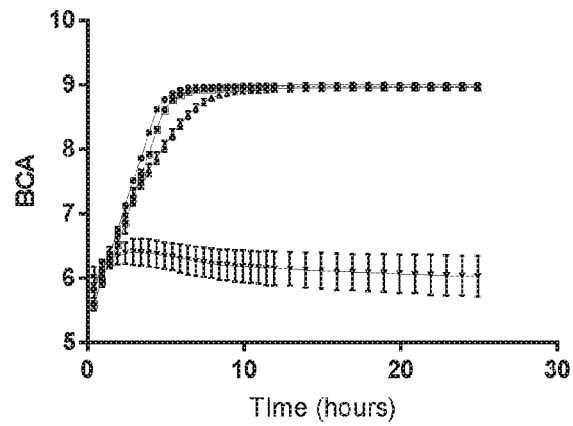
B
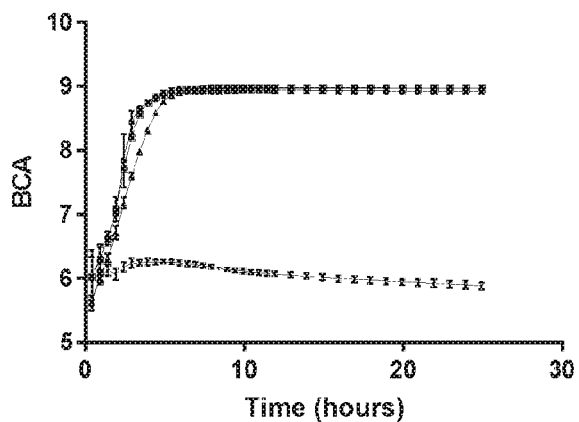
C
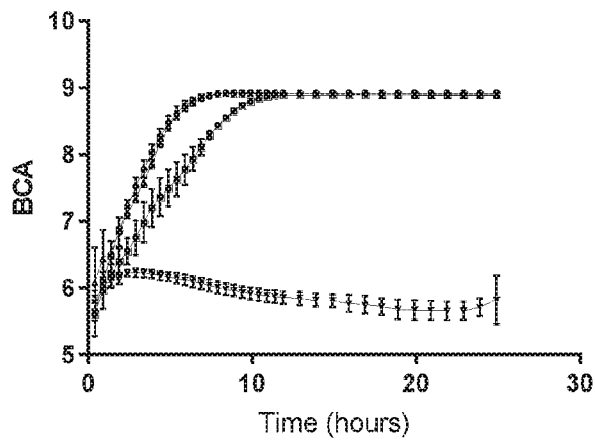
Fig. 2, continues

D
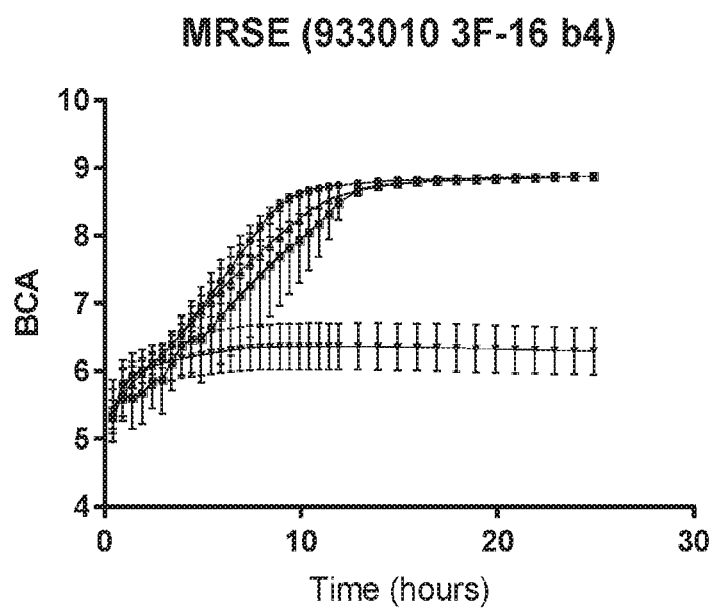
Fig. 2, continued

A
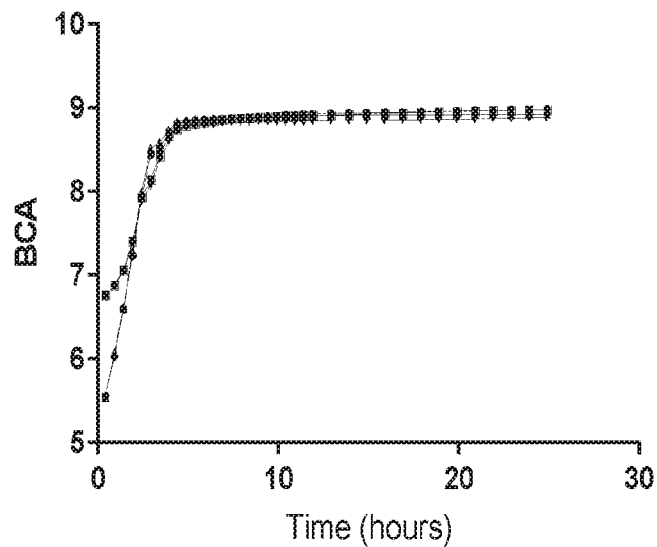
B
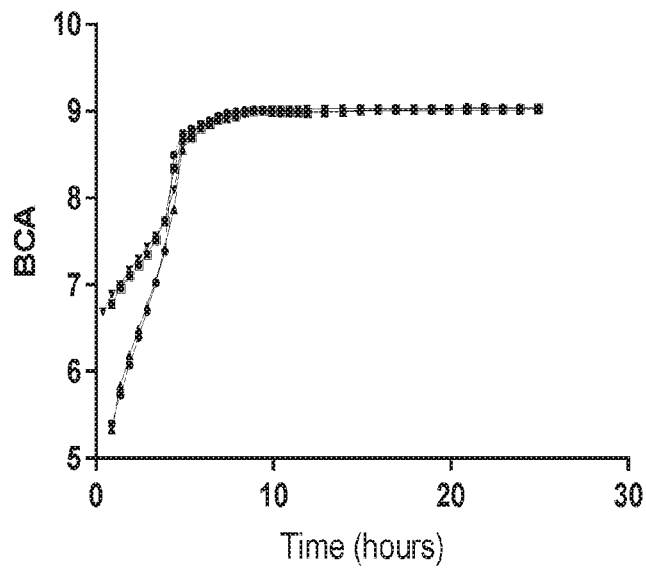
Fig. 3, continues

C
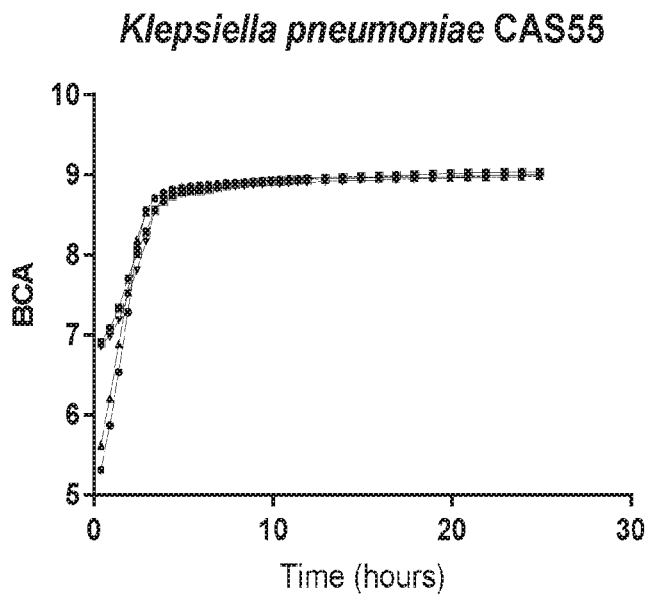
D
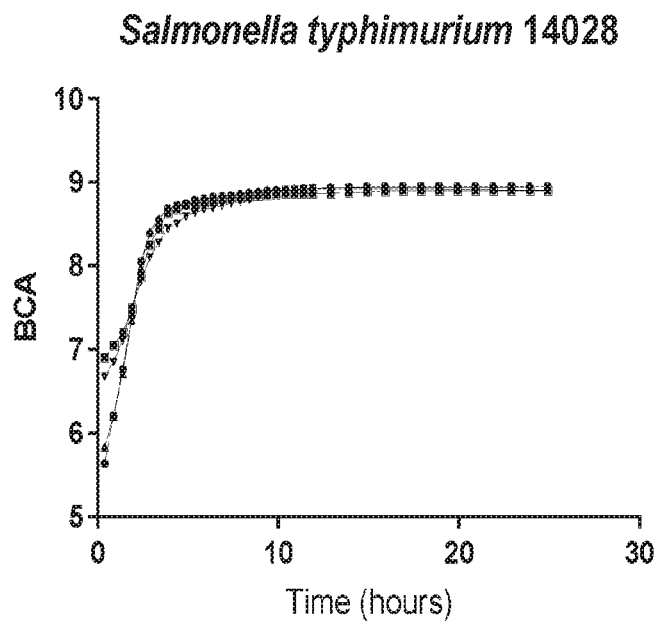
Fig. 3, continued

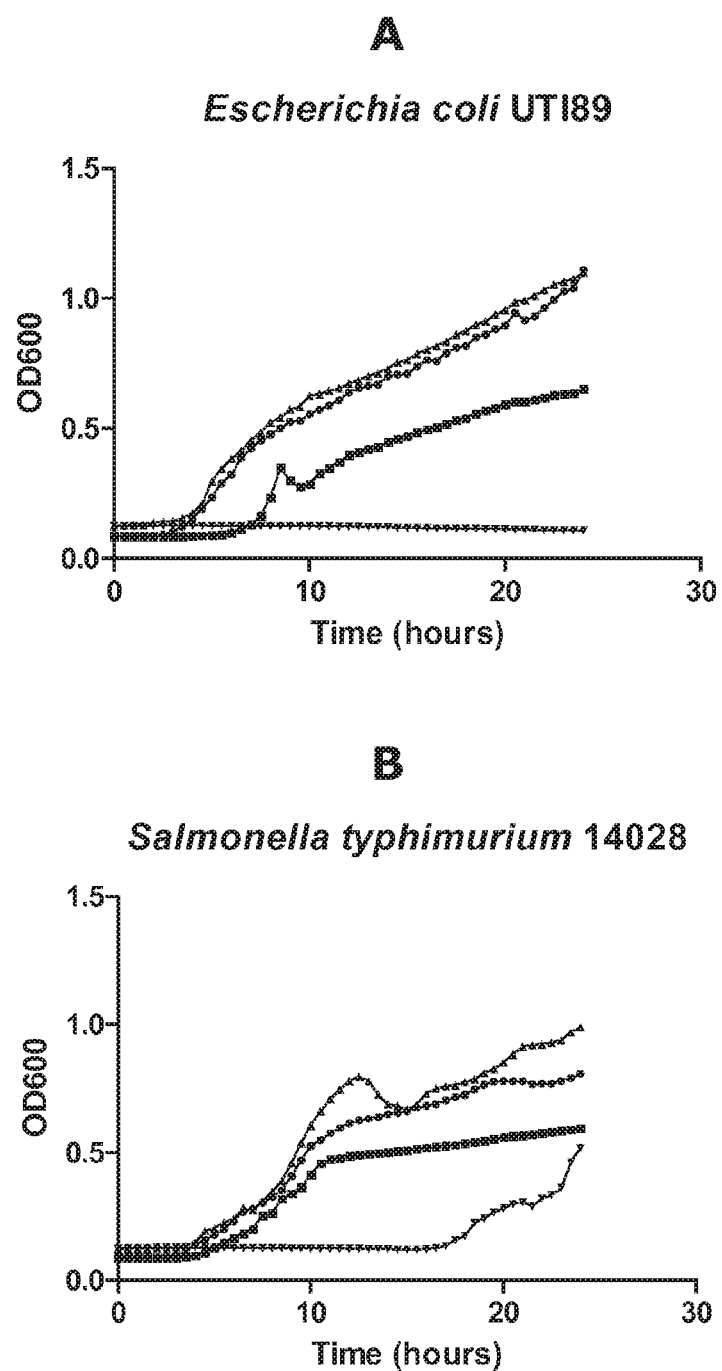
Fig. 5, continues

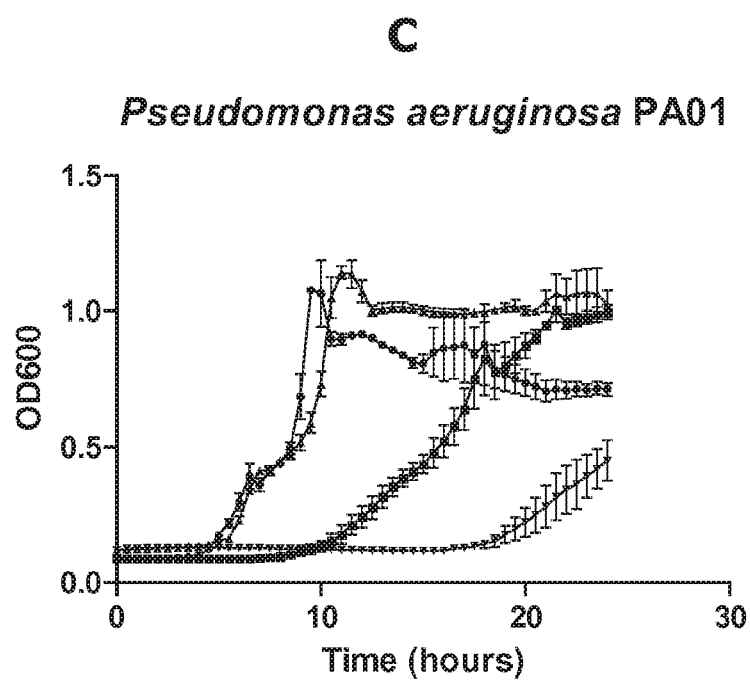
Fig. 5, continued

BACITRACIN AND/OR DAPTOMYCIN COMBINED WITH CANNABIDIOL FOR TREATMENT OF BACTERIAL INFECTIONS

CROSS REFERENCE TO RELATED APPLICATIONS

This is the U.S. National Stage of International Application No. PCT/EP2018/066234, filed Jun. 19, 2018, which was published in English under PCT Article 21(2), which in turn claims the benefit of European Application No. 17176612.4, filed Jun. 19, 2017, which is incorporated herein in its entirety.

TECHNICAL FIELD OF THE INVENTION

The present invention relates to combinatorial antibacterial compositions. In particular, the present invention relates to antibacterial compositions having a synergistic effect.

BACKGROUND OF THE INVENTION

Since the discovery of penicillin in 1928 by Sir Alexander Fleming, antibiotics have saved millions of lives worldwide. The causes of antibiotic resistance development have been known for a while, but the intent to solve the problem seems to be inadequate. Increasing demands for new antibacterial drugs have not been met due to growing numbers of multi drug resistant (MDR) bacteria. As development of new antimicrobial drugs is decreasing, we must turn to drugs which are already here.

This is where helper compounds come to use. Helper compounds are non-antibiotic compounds functioning as adjuvants for antibiotics to operate in synergy. Drugs found to contain helper compound properties were normally used for treatment of non-infectious diseases but might contain some degree of antibacterial activity itself. Since overuse of antibiotics is the main cause of antibiotic resistance, combining antibiotics with helper compounds would require less amount of antibiotic needed to achieve the same growth inhibition than seen when using higher concentration of the antibiotic alone and therefore decrease the likelihood of resistance development. Therefore, new helper compounds need to be found.

Cannabinoids may be categorized as either endogenous cannabinoids, which are cannabinoids produced by the human body, or exogenous cannabinoids which are produced either by plants such as *Cannabis sativa* or synthetically. Cannabinoids act on the endocannabinoid system of the human body consisting of two G-protein coupled receptors (GPCR). These are named cannabinoid type 1 and 2 (CB1 and CB2) receptors, and depending on the specific cannabinoid, the binding results in either an agonistic or antagonistic effect. Besides endocannabinoids being ligands for the endocannabinoid receptors, exogenous cannabinoids are also able to bind. One of the best characterized exogenous ligands is tetrahydrocannabinol (THC). It is a partial agonist for both CB1 and CB2 receptor mediating effects such as analgesia, muscle relaxation, and antiemetic effects, but also results in negative effects such as anxiety, psychosis, and sedation. Another exogenous cannabinoid is cannabidiol (CBD), which has been observed to decrease the adverse negative effects of THC. CBD is an antagonist of both CB1 and CB2 receptor leading to the anti-sedative, antipsychotic, and anxiolytic effects. Furthermore, it has been observed to inhibit growth of bacteria (Appendino G et al. Antibacterial cannabinoids from *Cannabis sativa*: A structure-activity study. Journal of Natural Products. 2008; 71(8):1427-30). However, the use of cannabidiol as an antibiotic adjuvant has not been studied so far.

Hence, improved or new helper compounds would be advantageous, and in particular more efficient and/or reliable new helper compounds would be advantageous.

SUMMARY OF THE INVENTION in here it is disclosed that cannabidiol (CBD) is a potential helper compound in the treatment of bacterial infections. CBD has been found to potentiate the effect of bacitracin and daptomycin against Gram-positive bacteria such as *Staphylococcus* species, *Listeria monocytogenes* and *Enterococcus faecalis* but not Gram-negative bacteria. Without being bound by theory, it is believed that CBD is capable of disrupt the membrane potential in *Staphylococcus aureus* and possibly inhibit the ATP synthase leading to potentiation of bacitracin. In addition, it is believed that by combining CBD and bacitracin, CBD is able to downregulate or decrease expression of bacitracin resistance genes leading to increased bacitracin concentration and effect. Together, these mechanisms result in a synergy between CBD and bacitracin enabling growth inhibition of resistant Gram-positive bacteria.

Based on these observations, the combination of CBD with bacitracin and/or daptomycin might be a putative novel treatment in future clinical settings for treatment of Gram-positive bacterial infections, and in particular, antibiotic resistant Gram-positive bacterial infections.

Furthermore, the present disclosure shows that the combination of CBD with kanamycin and/or polymyxin B might be a putative novel treatment in future clinical settings for treatment of Gram-negative bacterial infections.

Thus, an object of the present invention relates to the provision of multicomponent antibacterial compositions with synergistic effects.

In particular, it is an object of the present invention to provide a composition that solves the above-mentioned problems of the prior art with increased bacterial resistance against standard antibiotics.

Thus, one aspect of the invention relates to a composition comprising

Cannabidiol (CBD) or pharmaceutically acceptable salts thereof; and bacitracin or pharmaceutically acceptable salts thereof and/or daptomycin or pharmaceutically acceptable salts thereof.

Another aspect of the present invention relates to the composition according to the invention, for use as a medicament. Preferably, the composition is for use in the treatment and/or amelioration of Gram-positive bacterial infections.

Yet another aspect of the present invention relates to the use of a composition according to the invention for in vitro removal or prevention of growth of Gram-positive bacteria.

Yet a further aspect relates to a medical device (at risk of causing a bacterial infection in a subject) coated with or impregnated with a composition according to the invention.

Still another aspect of the present invention is to provide a kit of parts comprising a first container comprising Cannabidiol (CBD) or pharmaceutically acceptable salts thereof;

a second container comprising bacitracin or pharmaceutically acceptable salts thereof and/or daptomycin or pharmaceutically acceptable salts thereof; and optionally, instructions for use.

BRIEF DESCRIPTION OF THE FIGURES

FIG. 1 shows growth curves of CBD in combination with antibiotics in the resistant bacterium MRSA USA300. A: Combination of CBD 2 µg/mL with bacitracin 16 µg/mL, B: Combination of CBD 1 µg/mL with daptomycin 4 µg/mL, C: Combination of CBD 1 µg/mL with tetracycline 16 µg/mL, D and E: Combination of CBD 1 µg/mL with fosfomycin 16 and 8 µg/mL, F: Combination of CBD 1 µg/mL with dicloxacillin 0.0625, G: Combination of CBD 1 µg/mL with chlorhexidine 0.25 µg/mL, and H: Combination of CBD 1 µg/mL with vancomycin 0.5 µg/mL. BCA: Background corrected absorption. -●- Growth control, -■- CBD, -▲- Antibiotic, -▼- Combination.

FIG. 2 shows growth curves of CBD in combination with bacitracin in Gram-positive bacteria. A: *Enterococcus faecalis* (13-327129) CBD 2 µg/mL and bacitracin 16 µg/mL, B: *Enterococcus faecalis* (16-7418) 2 µg/mL and bacitracin 16 µg/mL, C: *Listeria monocytogenes* EGD CBD 2 µg/mL and bacitracin 32 µg/mL, D: MRSE (933010 3F-16 b4) CBD 2 µg/mL and bacitracin 4 µg/mL. BCA: Background corrected absorption. -●- Growth control, -■- CBD, -▲- Bacitracin, -▼- Combination.

FIG. 3 shows combination of CBD and bacitracin in Gram-negative bacteria. A: *Escherichia coli* UTI89, B: *Pseudomonas aeruginosa* PA01, C: *Klepsiella pneumoniae* CAS55 and D: *Salmonella typhimurium* 14028. BCA: Background corrected absorption. -●- Growth control, -■- CBD, -▲- Bacitracin, -▼- Combination. CBD 64 µg/mL and bacitracin 64 µg/mL.

FIG. 5 shows growth curves of CBD in combination with antibiotics in Gram-negative bacteria. A: *Escherichia coli* UTI89, 32 µg/mL CBD and 0.5 µg/mL Polymyxin B. B: *Salmonella typhimurium* 14028, 32 µg/mL CBD and 0.5 µg Polymyxin B. C: *Pseudomonas aeruginosa* PA01, 32 µg/mL CBD and 16 µg/mL Kanamycin. -●- Growth control, -■- CBD, -▲- Antibiotic, -▼- Combination.

Figure 4:
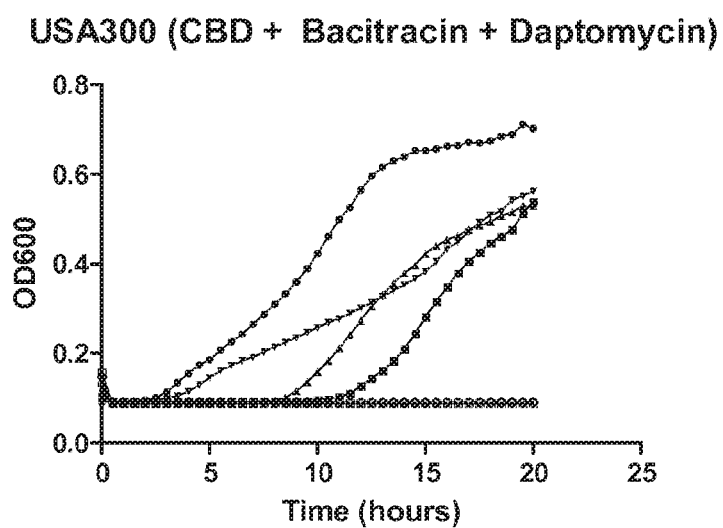
FIG. 4 shows growth curve of 2 µg/mL CBD, 16 µg/mL Bacitracin and 4 µg/mL Daptomycin in USA300. -●- Growth control, -■- CBD, -▲- Bacitracin, -▼- Daptomycin, -◇- CBD and Bacitracin, -○- CBD and Daptomycin, -□- CBD and Bacitracin and Daptomycin.

The present invention will now be described in more detail in the following.

DETAILED DESCRIPTION OF THE INVENTION

Definitions

Prior to discussing the present invention in further details, the following terms and conventions will first be defined:

Cannabidiol (CBD)

Cannabidiol (CBD) is one of at least 113 active cannabinoids identified in *Cannabis*. CBD does not appear to have any intoxicating effects such as those caused by THC in marijuana, but may have effects on anxiety and anti-psychotic effect.

Cannabidiol may have the CAS Registry Number 13956-29-1. Cannabidiol may also be in the form of a salt. Thus, the invention is also considered to cover pharmaceutically acceptable salts of Cannabidiol.

Bacitracin

Bacitracin is a mixture of related cyclic peptides produced by organisms of the licheniformis group of *Bacillus subtilis* var Tracy. These peptides disrupt gram positive bacteria by interfering with peptidoglycan biosynthesis.

Bacitracin is primarily used as a topical preparation. Bacitracin may have the CAS Registry Number: 1405-87-4. Bacitracin may also be in the form of a salt such as bacitracin zinc salt. Thus, the invention is also considered to cover pharmaceutically acceptable salts of bacitracin.

Daptomycin

Daptomycin is a lipopeptide antibiotic used in the treatment of systemic and life-threatening infections caused by Gram-positive organisms. It is a naturally occurring compound found in the soil saprotroph *Streptomyces roseosporus*. Its distinct mechanism of action makes it useful in treating infections caused by multiple drug-resistant bacteria. It is marketed in the United States under the trade name Cubicin by Cubist Pharmaceuticals.

Daptomycin may have the CAS Registry Number 103060-53-3. Daptomycin may also be in the form of a salt. Thus, the invention is also considered to cover pharmaceutically acceptable salts of Daptomycin.

Kanamycin

Kanamycin A, often referred to simply as kanamycin, is an antibiotic used to treat severe bacterial infections and tuberculosis. Kanamycin may have the CAS Registry Number 59-01-8.

Polymyxins

Polymyxins are antibiotics. Polymyxins B and E (Polymyxins E is also known as colistin) are used in the treatment of Gram-negative bacterial infections. They work mostly by breaking up the bacterial cell membrane.

Compositions

As described above, the present invention relates to compositions displaying synergistic effects when it comes to treating gram-positive bacterial infections. Thus, in a first aspect the invention relates to a composition comprising Cannabidiol (CBD) or pharmaceutically acceptable salts thereof; and bacitracin or pharmaceutically acceptable salts thereof and/or daptomycin or pharmaceutically acceptable salts thereof.

As shown in example 1, the combination of Cannabidiol with either bacitracin or daptomycin shows a synergistic effect in inhibiting Gram-positive growth (MRSA). Such effect could not be found when Cannabidiol were combined with other tested antibiotics. Similarly, other members of the cannabinoid family did not show a synergistic effect when combined with either bacitracin or daptomycin (Example 4).

Thus, in preferred aspect the invention relates to a composition comprising

Cannabidiol (CBD) or pharmaceutically acceptable salts thereof; and bacitracin or pharmaceutically acceptable salts thereof.

In an embodiment, the composition further comprises daptomycin or pharmaceutically acceptable salts thereof.

In an additional aspect, it is to be understood that the invention also relates to a composition comprising Cannabidiol (CBD) or pharmaceutically acceptable salts thereof; and functional equivalents to bacitracin or pharmaceutically acceptable salts thereof.

In an embodiment, the functional equivalents to bacitracin is selected from the group consisting of Viridicatumtoxin, Spirohexaline, and Plantaricin C. Viridicatumtoxin and Spirohexaline, are small fungal molecules with a tetracyclic scaffold and an additional spirobicyclic ring in common. They were were found to inhibit bacterial undecaprenyl pyrophosphate (UPP) synthase with IC50 values of 4 and 9

µM, respectively. They showed antimicrobial activity, particularly against Gram-positive bacteria including methicillin-resistant *Staphylococcus aureus* (MRSA). Furthermore, molecular modeling strongly suggested that the hydrophobic spirobicyclic ring of viridicatumtoxin interacts with three hydrophobic clefts of the active site in MRSA UPP synthase (The Journal of Antibiotics volume 69, pages 798-805 (2016)). Plantaricin C (PlnC) falls into the category of lipid II-interacting antimicrobial peptides and acts as a potent cell wall synthesis inhibitor. PlnC shares intermediate features with the prototype lantibiotics raisin and mersacidin concerning both its structure and lipid II interaction, which are also reflected in its biological activity (Appl Environ Microbiol. 2006 April; 72(4): 2809-2814).

In yet a preferred aspect the invention relates to a composition comprising
  Cannabidiol (CBD) or pharmaceutically acceptable salts thereof; and
  Daptomycin or pharmaceutically acceptable salts thereof.

In an embodiment, the composition further comprises bacitracin or pharmaceutically acceptable salts thereof.

In an additional aspect, the invention relates to a composition comprising
  Cannabidiol (CBD) or pharmaceutically acceptable salts thereof; and
  Kanamycin or pharmaceutically acceptable salts thereof.

Example 6 shows preliminary data indicating a synergistic effect of the combination of CBD and kanamycin on the Gram-negative bacteria *Pseudomonas aeruginosa*.

In yet an additional aspect, the invention relates to a composition comprising
  Cannabidiol (CBD) or pharmaceutically acceptable salts thereof; and
  Polymyxin (such as polymyxin B or E) or pharmaceutically acceptable salts thereof.

Example 6 shows preliminary data indicating a synergistic effect of the combination of CBD and polymyxin B on the gram-negative bacteria *Escherichia coli* and *Salmonella typhimurium*. Thus, Polymyxin B is preferred. In an embodiment the composition comprises
  0.1 µg/mL-50 mg/ml CBD or pharmaceutically acceptable salts thereof; and
  0.1 µg/mL-50 mg/ml Polymyxin or pharmaceutically acceptable salts thereof. In yet an embodiment the composition comprises
  0.1 µg/mL-50 mg/ml CBD or pharmaceutically acceptable salts thereof; and
  0.1 µg/mL-50 mg/ml kanamycin or pharmaceutically acceptable salts thereof.

The composition(s) may contain different amounts of each component depending on the desired use. The exact concentrations in the composition will of course depend on the type of administration when used as a medicament. For example, concentrations for e.g. intravenous application will likely differ from compositions designed for topical application. Similarly, the concentrations may differ depending on an in vitro use, e.g. coating or impregnation of medical devices. Thus, in an embodiment, the composition comprises at least 0.0001 µg/ml CBD or pharmaceutically acceptable salts thereof, such as in the range 0.0004 µg/ml-100 mg/ml, such as in the range 0.004 µg/ml-50 mg/ml, such as in the range 0.04 µg/ml-30 mg/ml, preferably in the range 0.1 µg/ml-30 mg/ml and even more preferably 0.1 µg/ml-10 mg/ml.

In another embodiment, the composition comprises at least 0.0001 µg/ml bacitracin or pharmaceutically acceptable salts thereof, such as in the range 0.0004 µg/ml-100 mg/ml, such as in the range 0.004 µg/ml-50 mg/ml, such as in the range 0.04 µg/ml-30 mg/ml, preferably in the range 0.1 µg/ml-30 mg/ml, and even more preferably 0.1 µg/ml-10 mg/ml.

In yet an embodiment, the composition comprises at least 0.0001 µg/ml daptomycin or pharmaceutically acceptable salts thereof, such as in the range 0.0004 µg/ml-200 mg/ml, such as in the range 0.004 µg/ml-100 mg/ml, such as in the range 0.04 µg/ml-50 mg/ml, preferably in the range 1 mg/ml-50 mg/ml and even more preferably 10 mg/ml-50 mg/ml.

In yet a further embodiment the composition comprises
  0.1 µg/mL-50 mg/ml CBD or pharmaceutically acceptable salts thereof; and
  0.1 µg/mL-50 mg/ml bacitracin or pharmaceutically acceptable salts thereof.

In an embodiment the composition comprises
  0.1 µg/mL-50 mg/ml CBD or pharmaceutically acceptable salts thereof; and
  0.1 µg/mL-50 mg/ml daptomycin or pharmaceutically acceptable salts thereof.

The composition may be provided in different forms, depending on the specific use. Thus, in an embodiment, the composition is in the form of a solution, tablet, crème, a lotion, a gel, an ointment, an ophthalmic solution, an ophthalmic ointment, an intramuscular solution. For topical application crèmes, lotions, and gels may be specifically useful.

The composition may also comprise further components. Thus, in an embodiment the composition further comprises a diluent, an adjuvant, and/or a pharmaceutical acceptable carrier.

The composition may also be further optimized to improve delivery. Thus, in an embodiment the Cannabidiol (CBD) or pharmaceutically acceptable salts thereof, the bacitracin or pharmaceutically acceptable salts thereof and/or daptomycin or pharmaceutically acceptable salts thereof are in a carrier or an encapsulating vehicle, such as a liposome, or a nanoliposome.

The compositions according to the invention are preferably free from the principal psychoactive constituents of *Cannabis*. Thus, in an embodiment, the composition comprises less than 0.1% (w/w) Tetrahydrocannabinol (THC), such as less than 0.01%, such as less than 0.001%, such as less than 0.0001%, or such as being free or substantially free from THC.

The composition may also comprise further components to improve the antimicrobial effect. Thus, in an embodiment, the composition further comprises one or more additional antibiotics, such as polymyxin B or salts thereof and/or neomycin or salts thereof. Bacitracin (as bacitracin zinc salt), in combination with other topical antibiotics (usually polymyxin B and neomycin) is sold as an ointment ("triple antibiotic ointment," with a common brand name Neosporin), it is used for topical treatment of a variety of localized skin and eye infections, as well as for the prevention of wound infections. A non-ointment form of ophthalmic solution is also available for eye infections.

In yet an embodiment the composition further comprising zinc, cobalt, nickel, cobber calcium, and/or other metal ions. These components may improve the functionality of the active compounds in the composition.

The compositions may also be optimized for skin application. Thus, in an embodiment the composition comprises a lubricant and/or a moisture insulator such as Vaseline.

As mentioned above CBD is naturally present in *Cannabis* and may be isolated therefrom. However, CBD may also be provided from other sources. Thus, in a further embodiment, cannabidiol is derived/purified from the hemp plant, produced in a microorganism or is chemically synthesized.

As is clear from the above, the compositions according to the invention may be used as a medicament. Thus, in yet an embodiment the composition is a pharmaceutical composition.

Compositions for Medical Use

The compositions according to the invention may find use as a medicament. Thus, an aspect of the invention relates to the composition according to the invention, for use as a medicament.

In an embodiment, the composition is for use in the treatment and/or growth inhibition of Gram-positive bacterial infections (with the provision that the composition comprises CBD+Bacitracin and/or CBD+Daptomycin). As shown in examples 2 and 5, the compositions comprising CBD+Bacitracin, CBD+Daptomycin and CBD+Daptomycin+Bacitracin are efficient in inhibiting growth of Gram-positive bacteria, whereas the compositions are inefficient in inhibiting growth of Gram-negative bacteria (example 3).

In yet an embodiment, the Gram-positive bacterial infection is selected from the group consisting of MRSA (Methicillin-Resistant *Staphylococcus aureus*), *Enterococcus faecalis*, Methicillin-Resistant *Staphylococcus epidermidis* (MRSE), *Listeria monocytogenes, Streptococcus pyogenes, Streptococcus pneumonia, bacillus, clostridium, streptococcus, Corynebacterium* or combinations thereof.

In another embodiment, the composition is use in the treatment and/or prevention of growth of Gram-negative bacterial infections (with the proviso that the composition comprises (CBD+kanamycin and/or CBD+polymyxins), such as *Pseudomonas*, e.g. *Pseudomonas aeruginosa, Escherichia coli, Salmonella*, such as *Salmonella typhimurium*. As shown in example 6, CBD+Kanamycin and CBD+Polymyxins are efficient against Gram-negative bacteria.

In yet a further embodiment, the bacterial infections to be treated are considered resistant to one or more antibiotics. If considered resistant to more than one antibiotic such bacteria may be considered multi-resistant.

In yet another embodiment, the composition is for use in the treatment of skin infections, such as psoriasis or impetigo, wound infections, burns. In a related embodiment, the composition is for topical application, such as on the skin, e.g. at or near wounds or an infected site.

In yet another embodiment, the composition is for use in the treatment of eye infections. In a related embodiment, the composition is for ophthalmic application (eye application).

The composition may be applied to both humans and animals. Thus, in an embodiment the use is for mammals, such as humans, pet animals, such as cats and dogs, or farm animals, such as cows, horses and pigs.

In Vitro Uses

The compositions according to the invention may also find use in vitro. Thus, an aspect of the invention relates to the use of a composition according to the invention for in vitro removal or in vitro prevention of growth of Gram-positive bacteria (with the proviso that the composition comprises CBD+Bacitracin and/or CBD+Daptomycin).

In another aspect of the invention relates to the use of a composition according to the invention for in vitro removal or in vitro prevention of growth of Gram-negative bacteria (with the proviso that the composition comprises CBD+kanamycin and/or CBD+polymyxins).

In an embodiment, the in vitro use is for removal of bacteria from surfaces, or for preventing colonization/growth of bacteria on surfaces, such as surfaces on prostheses or medical devices, such as catheters and implants. Such removal may be relevant before the medical devices are taken into use.

A further aspect relates to the use of a composition according to the invention for coating or impregnating a medical device. This could be relevant to prevent colonization of medical devices at risk of causing a bacterial infection in a subject. Such devices could be catheters, prostheses, and implants.

Yet a further aspect relates to a medical device (at risk of causing a bacterial infection in a subject) coated with or impregnated with a composition according to the invention. Again, such device could be catheters, prostheses, and implants.

Kit of Parts

Since the compositions according to the invention is multicomponent compositions, it can be envisioned that the composition could be provided as a kit of parts. Thus, an aspect of the invention relates to a kit of parts comprising
 a first container comprising Cannabidiol (CBD) or pharmaceutically acceptable salts thereof;
 a second container comprising bacitracin or pharmaceutically acceptable salts thereof and/or daptomycin or pharmaceutically acceptable salts thereof; and
 optionally, instructions for use.

The concentrations described for the composition according to the invention finds equal applicability to the kit of the invention.

In a further aspect, the invention relates to a kit of parts according to the invention for use as a medicament.

As mentioned above, said use could be for treating Gram-positive bacterial infections, which may cause diseases such as skin infections, such as psoriasis or impetigo, wound infections, burns, and/or eye infections.

Yet an aspect of the invention relates to a kit of parts comprising
 a first container comprising Cannabidiol (CBD) or pharmaceutically acceptable salts thereof;
 a second container comprising Kanamycin or pharmaceutically acceptable salts thereof and/or Polymyxin or pharmaceutically acceptable salts thereof; and
 optionally, instructions for use.

The concentrations described for the compositions according to the invention finds equal applicability to the kit of the invention.

In a further aspect, the invention relates to a kit of parts according to the invention for use as a medicament. As mentioned above, said use could be for treating Gram-negative bacterial infections, which may cause diseases/infections.

Further Aspects

In yet an aspect, the invention relates to a method for treating, preventing growth of or ameliorating a Gram-positive bacterial infection in a subject, the method comprising administering a composition according to the invention to the subject, such as by topical administration. The components of the composition may be administered simultaneously or after each other. It is to be understood that this aspect relates to the compositions comprising Bacitracin and/or Daptomycin as outlined above.

In yet another aspect, the invention relates to a method for treating, preventing growth of or ameliorating a Gram-negative bacterial infection in a subject, the method comprising administering a composition according to the invention to the subject, such as by topical administration. The components of the composition may be administered simultaneously or after each other. It is to be understood that this aspect relates to the compositions comprising kanamycin and/or polymyxin as outlined above.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

Combining Cannabidiol with Antibiotics

Aim of Study

Characterization of cannabidiol (CBD) as a potential helper compound.

Materials and Methods

Bacteria and Growth Conditions

The resistant bacterium MRSA USA300 FPR3757 (USA300) was the main used bacterium throughout this study. MRSA was grown in Brain Heart Infusion (BHI) or Müeller Hinton (MH) media on plate or in liquid cultures with agitation at 37° C.

Additional bacteria *Enterococcus faecalis* (13-327129), *Enterococcus faecalis* (16-7418), Methicillin-resistant *Staphylococcus epidermidis* (933010 3F-16 b4), *Listeria monocytogenes* EGD, *Pseudomonas aeruginosa* (PA01), *Salmonella typhimurium* (14028), *Klepsiella pneumoniae* (CAS55), *Vibrio cholerae* (A1522), and *Escherichia coli* (UTI89) were either grown in BHI or Lysogeny broth (LB) media.

Minimum Inhibitory Concentration (MIC) and Fractional Inhibitory Concentration (FIC) Index An ON culture was made by inoculating a bacterial colony in either 5 mL of MH or BHI and incubating at 37° C. with agitation. The antibiotic of interest was added to a row of a sterile 96-well plate (VWR) and a serial dilution was made down the rows containing 50 µL of MH or BHI media in each well, resulting in 2-fold dilution for each row. The ON culture was diluted to $OD_{625}$ at approximately 1.0 followed by a 1:100 dilution to approximately $OD_{625}$=0.01 of which 50 µL was added to each well to a final volume of 100 µL. The 96-well plate was incubated at 37° C. with shaking at 225 rpm for approximately 18-24 hours. Presence and absence of growth were determined by visual appearance. FIC index was calculated as follows (Alam M T et al. Antibacterial activity of different organic extracts of *Achyranthes aspera* and *Cassia alata*. J Sci Res. 2009).

$$FIC\ index = \frac{MIC\ of\ compound\ A\ in\ combination\ with\ compound\ B}{MIC\ of\ compound\ A\ alone} + \frac{MIC\ of\ compound\ B\ in\ combination\ with\ compound\ A}{MIC\ of\ compound\ B\ alone}$$

Micro Dilution Growth Experiments Using Philips oCelloScope System

An ON culture was made by inoculating a bacterial colony in either 5 mL of MH or BHI at incubated at 37° C. with agitation. 25 µL of specific concentrations of the antibiotic and cannabinoid to be tested was added to the desired wells of a sterile 96-well plate (Thermo Scientific). 25 µL of MH or BHI media was added to the wells only containing one of the two compounds tested. The bacterial ON culture was diluted to a final $OD_{600}$ nm of 0.005 and 50 µL was dispensed into each well to a final volume of 100 µL. To decrease evaporation, 2 mL of pre-heated water was added to the corners of the 96-well plate containing cavities. The plate was placed in the oCelloScope inside an incubator at 37° C. Illumination level and focus was adjusted for each well and the growth was measured for approximately 25 hours. Measurements were performed every half an hour for the first half of the time and every hour for the last half using the UniExplorer software. Data retrieved was given in Background corrected absorption (BCA), formerly known as pixel histogram summation (PHS), an algorithm enabling determination of bacterial growth kinetics resulting from images taken with the oCelloScope camera.

In order to characterize cannabidiol as a potential helper compound, two separate screens were performed using the chequerboard setup.

A) A screen was performed using the Philips oCelloScope enabling measurements of bacterial growth in presence or absence of either cannabidiol alone or in combination with an antibiotic or antimicrobial, through a 3D scanning system in 96-well plates. The various antibiotics tested during the screens are listed in table 1 with their corresponding MIC values for USA300.

The concentrations of the compounds tested, including CBD were at 0.5×, 0.25×, and 0.125×MIC values. Growth curves yielding the best growth inhibition in combination without causing too much inhibition in monotherapy are visualized in FIG. 1.

B) The other screen was based on fractional inhibitory concentration (FIC) index. Calculation of the FIC index enables a direct and quantitative way of characterizing synergy between two compounds whereas the other screen only resulted in indications of synergy. Thus, trough calculation of the FIC index, one can visualize if synergy is observed between two compounds or not. Synergy was defined as described by Odds (Odds F C. Synergy, antagonism, and what the chequerboard puts between them. Journal of Antimicrobial Chemotherapy. 2003; 52(1)), a FIC index above 4 defines antagonism, a FIC index between 0.5 and 4.0 defines no interaction and a FIC index below or equal to 0.5 defines synergy.

Results

FIG. 1 shows a synergistic potential for the combination of cannabidiol with the cyclic peptide antibiotic bacitracin (BAC) (FIG. 1A) and to some degree daptomycin (DAP) (FIG. 1B), tetracycline (TET) (FIG. 1C), and fosfomycin (FOS) (FIG. 1D). However, lower concentration of fosfomycin (FIG. 1E) shows an antagonistic potential when combined with cannabidiol. Combination of CBD with either dicloxacillin (DCX) (FIG. 1F), chlorhexidine (CHX) (FIG. 1G) or vancomycin (VAN) (FIG. 1H) show no synergistic potential.

TABLE 1

MIC values and FIC indices for cannabidiol and the various antimicrobials in USA300. FIC indices are indicated for the combination of cannabidiol with the respective antibiotic.

| | WT USA300 | |
| --- | --- | --- |
| Compound tested | MIC (µg/mL) | FIC Index |
| Cannabidiol (CBD) | 4 | |
| Dicloxacillin | 0.25 | 2 |

TABLE 1-continued

MIC values and FIC indices for cannabidiol and the various antimicrobials in USA300. FIC indices are indicated for the combination of cannabidiol with the respective antibiotic.

| Compound tested | WT USA300 MIC (μg/mL) | FIC Index |
|---|---|---|
| Vancomycin | 2.0 | 2 |
| Daptomycin | 16 | 0.38 |
| Bacitracin | 64 | 0.30 |
| Chlorhexidine | 1-2 | 1 |
| Tetracycline | 64 | 1 |
| Fosfomycin | 32 | . . . |
| Nisin | 256 | 2 |
| Ceftriaxone | 32 | 1.5 |

Remarkably, as visualized in table 1, both daptomycin and bacitracin when combined with CBD, show FIC indices below 0.5, indicating synergy, whereas dicloxacillin, vancomycin, chlorhexidine, tetracycline, nisin or ceftriaxone had a FIC index of 1 or above when combined with CBD indicating no synergy when combined with cannabidiol.

Conclusion

These results indicate synergy between the combination of CBD with both bacitracin and daptomycin. However, since bacitracin showed better synergy in both screens, bacitracin was chosen for further studies.

Example 2

Combination of CBD and Bacitracin on Different Strains of Gram-Positive Bacteria Aim of Study To study the bacterial spectrum of the combination of CBD and bacitracin on Gram-positive bacteria.

Materials and Methods

To study the bacterial spectrum of the combination, CBD and bacitracin growth measurements of other Gram-positive bacteria tests on *Enterococcus faecalis*, an MRSE strain and a strain of *Listeria monocytogenes* were performed as described in Example 1.

Results

The MIC for bacitracin and CBD and the respective FIC values are visualized in table 2 for the Gram-positive bacteria and are calculated based on two biological replicates.

TABLE 2

MIC values for CBD and bacitracin in Gram-positive bacteria and the respective FIC indices when combining CBD and bacitracin. In addition, fold decreased MIC value for bacitracin when combined with CBD compared to MIC value for bacitracin alone is indicated as well.

| Gram-positive strains tested | Cannabidiol MIC (μg/mL) | Bacitracin MIC (μg/mL) | FIC index | Fold decreased bacitracin |
|---|---|---|---|---|
| MRSA USA300 FPR3757 | 4 | 64 | 0.30 | 16-32 |
| E. faecalis (13-327129) | 16 | 128 | 0.13 | 16 |
| E. faecalis (16-7418) | 16 | 128 | . . . | . . . |
| MRSE (933010 3F-16 b4) | 4 | 32 | 0.14 | 64 |
| L. monocytogenes EGD | 4 | 512 | 0.34 | 8-16 |

Remarkably, all strains show FIC indices below 0.5 for the combination of bacitracin and CBD. Furthermore, the fold decreased bacitracin MIC when combined with CBD compared to MIC of bacitracin alone is indicated as well, and show great reduction in MIC value.

Growth experiments using the oCelloScope were performed as well for the Gram-positive bacteria. As expected, these growth experiments confirmed the advantageous synergy between CBD and bacitracin as well (FIG. 2).

Conclusion

These observations indicate that the synergy between CBD and bacitracin is applied for different types of Gram-positive bacteria.

Example 3

Combination of CBD and Bacitracin on Different Strains of Gram-Negative Bacteria Aim of Study To study the bacterial spectrum of the combination of CBD and bacitracin on Gram-negative bacteria.

Materials and Methods

To further assess the spectrum of use for the combination of CBD and bacitracin, growth of Gram-negative bacteria upon treatment was measured as well as described in Example 1.

The Gram-negative bacteria tested were strains of *Pseudomonas aeruginosa*, *Salmonella typhimurium*, *Klepsiella pneumoniae*, *Vibrio cholera*, and *Escherichia coli*. MIC for CBD and bacitracin in the Gram-negative bacteria are visualized in table 3, and were both above tested concentrations.

TABLE 3

MIC values of CBD and bacitracin in Gram-negative bacteria. Exact MIC values were not found for either of the compounds, as it was above tested concentrations.

| Bacterial strain | MIC of CBD (μg/mL) | MIC of Bacitracin (μg/mL) |
|---|---|---|
| *Pseudomonas aeruginosa* (PA01) | >128 | >1024 |
| *Salmonella typhimurium* (14028) | >128 | >1024 |
| *Klepsiella pneumoniae* (CAS55) | >128 | >1024 |
| *Vibrio cholerae* (A1522) | >128 | >1024 |
| *Escherichia coli* (UTI89) | >128 | >1024 |

Furthermore, growth experiments for all gram-negative strains (FIG. 3) indicate no synergy between CBD and bacitracin.

Conclusion

The tested growth experiments for all gram-negative strains indicate no synergy between CBD and bacitracin, limiting the use of the combination to only Gram-positive bacteria.

Example 4

Synergy for Other Members of the Cannabinoid Family

Aim of Study

To investigate if the synergy is applied for other members of the cannabinoid family.

Materials and Methods

Cannabigerol (CBG) and cannabichromene (CBC) were studied in combination with either bacitracin or daptomycin against USA300. Both MIC and FIC indices are listed in table 4.

TABLE 4

MIC values of cannabigerol and cannabichromene in USA300 and the FIC indices when combined with either bacitracin or daptomycin.

| Compound tested | MIC | FIC index (with bacitracin) | FIC index (with daptomycin) |
|---|---|---|---|
| Cannabigerol (CBG) | 4 | 0.88 | 1.0 |
| Cannabichromene (CBC) | 4 | 0.63 | 0.63 |

Despite similar MIC values for CBG and CBC compared to CBD in MRSA USA300, FIC indices show no synergy for the use of either CBG or CBD, as they were above 0.5.

Conclusion

The combination of bacitracin with other cannabinoids did not result in synergy, indicating that a very rare synergy has been identified.

Summary of Experiments

Through growth experiments, it was surprisingly found that CBD was able to potentiate the effects of both bacitracin and daptomycin in *S. aureus* USA300. The combination of CBD and bacitracin was found only to be applicable for Gram-positive bacteria and not Gram-negative bacteria. In addition, the combination was limited to the use of cannabidiol as the other cannabinoids tested, showed FIC indices below the threshold of synergy.

In sum, a very specific synergistic effect for combinations of a certain cannabinoid and selected antibiotics in relation to growth inhibition of Gram-positive bacterial strains has been identified.

Example 5

Triple Combination of CBD, Daptomycin and Bacitracin on the Gram-Positive Bacteria *Staphylococcus aureus*

Aim of Study

To study the bacterial spectrum of the combination of CBD, daptomycin and bacitracin on the Gram-positive bacteria *Staphylococcus aureus*.

Materials and Methods

Micro Dilution Growth Experiments Using Synergy H1 Microplate Reader

On day one, a colony grown on an LB or an MH plate was inoculated in 5 mL of MH media at 37° C. The next clay, the ON culture was diluted to OD600=0.1 in MH media and then further diluted 100 times in MH media to an OD600 of approximately 0.001. 50 µL of the bacterial culture was added to wells in a 96-well plate containing CBD or an antibiotic, prepared as mentioned above to a final volume of 100 µL. The plate was placed in a Synergy H1 Microplate reader and optical density measurements were performed every 30 minutes with 15 seconds shaking before every measurement for 24 hours at 37° C.

Results

FIG. 4 shows a synergistic potential for the combination of cannabidiol with bacitracin and daptomycin at the same level of synergy as the combination of CBD and bacitracin.

Conclusion

The presented data shows efficient growth inhibition of Gram-positive bacterial strains using a triple combination of CBD, daptomycin and bacitracin.

Example 6

CBD Together with Kanamycin on *Pseudomonas aeruginosa* and CBD Together with Polymyxin B on *Salmonella typhimurium* and on *Escherichia coli*

Aim of Study

To study the bacterial spectrum of the combination of CBD and kanamycin on the Gram-negative bacteria *Pseudomonas aeruginosa* and the combination of CBD and polymyxin B on *Salmonella typhimurium* and *Escherichia coli*.

Materials and Methods

Micro dilution growth experiments using Synergy H1 Microplate reader as described above.

Results

FIG. 5 shows a synergistic potential for the combination of Cannabidiol (CBD) with kanamycin and the combination of cannabidiol with polymyxin B on *Salmonella typhimurium* and *Escherichia coli*. The effect observed seems to be synergistic but not to the same extent as CBD and bacitracin against MRSA.

Conclusion

Preliminary data indicate a synergistic effect of CBD together with kanamycin on *Pseudomonas aeruginosa* and of CBD together with Polymyxin B on *Salmonella typhimurium* and on *Escherichia coli*.

The invention claimed is:

1. A composition comprising:
   (a) cannabidiol (CBD) or pharmaceutically acceptable salts thereof; and
   (b) bacitracin or pharmaceutically acceptable salts thereof and/or daptomycin or pharmaceutically acceptable salts thereof.

2. The composition of claim 1, wherein the composition is in the form of a solution, a crème, a lotion, a gel, an ointment, an ophthalmic solution, an ophthalmic ointment, or a tablet.

3. The composition of claim 1, further comprising zinc, cobalt, nickel, cobber calcium, and other metal ions.

4. The composition of claim 1, comprising less than 0.1% (w/w) tetrahydrocannabinol (THC).

5. The composition of claim 1, comprising:
   (a) cannabidiol (CBD) or pharmaceutically acceptable salts thereof; and
   (b) bacitracin or pharmaceutically acceptable salts thereof.

6. The composition of claim 1, comprising:
   (a) cannabidiol (CBD) or pharmaceutically acceptable salts thereof; and
   (b) daptomycin or pharmaceutically acceptable salts thereof.

7. The composition of claim 1, comprising:
   (a) 0.1 µg/mL-50 mg/ml CBD or pharmaceutically acceptable salts thereof; and (b) 0.1 µg/mL-50 mg/ml bacitracin or pharmaceutically acceptable salts thereof.

8. The composition of claim 1, comprising:
   (a) 0.1 µg/mL-50 mg/ml CBD or pharmaceutically acceptable salts thereof; and
   (b) 0.1 µg/mL-50 mg/ml daptomycin or pharmaceutically acceptable salts thereof.

9. The composition of claim 1, wherein the composition is coated or impregnated on a medical device.

10. The composition of claim 1, wherein the composition is coated or impregnated on a medical device selected from the group consisting of catheters, prostheses, and implants.

11. A method for treating, preventing growth of, or ameliorating a Gram-positive bacterial infection in a subject, comprising administering to the subject a composition, comprising:
    (a) cannabidiol (CBD) or pharmaceutically acceptable salts thereof; and
    (b) bacitracin or pharmaceutically acceptable salts thereof and/or daptomycin or pharmaceutically acceptable salts thereof.

12. The method of claim 11, wherein the composition is topically administered.

13. The method of claim 11, wherein the composition is ophthalmically administered.

14. The method of claim 11, wherein the Gram-positive bacterial infection in a subject is selected from the group consisting of skin infections, psoriasis impetigo, wound infections, burns, and eye infections.

15. The method of claim 11, wherein the Gram-positive bacterial infection is selected from the group consisting of MRSA (Methicillin-Resistant *Staphylococcus aureus*), *Enterococcus faecalis*, Methicillin-Resistant *Staphylococcus epidermidis* (MRSE), *Listeria monocytogenes, Streptococcus pyogenes, Streptococcus pneumonia, Bacillus, Clostridium, Streptococcus, Corynebacterium*, and combinations thereof.

16. The method of claim 11, wherein the composition comprises:
    (a) cannabidiol (CBD) or pharmaceutically acceptable salts thereof; and
    (b) daptomycin or pharmaceutically acceptable salts thereof.

17. A method for treating, preventing growth of, or ameliorating a Gram-negative bacterial infection in a subject, comprising administering to the subject a composition, comprising:
    (a) cannabidiol (CBD) or pharmaceutically acceptable salts thereof; and
    (b) kanamycin or pharmaceutically acceptable salts thereof, and/or polymyxins or pharmaceutically acceptable salts thereof.

18. The method of claim 17, wherein the Gram-negative bacterial infection is selected from the group consisting of *Pseudomonas, Escherichia coli*, and *Salmonella*.

19. The method of claim 17, wherein the composition is topically administered.

20. The method of claim 17, wherein the Gram-negative bacterial infection in a subject is selected from the group consisting of skin infections, psoriasis impetigo, wound infections, burns, and eye infections.

* * * * *